United States Patent
Cases et al.

(10) Patent No.: US 7,701,222 B2
(45) Date of Patent: Apr. 20, 2010

(54) METHOD FOR VALIDATING PRINTED CIRCUIT BOARD MATERIALS FOR HIGH SPEED APPLICATIONS

(75) Inventors: Moises Cases, Austin, TX (US); Bradley Donald Herrman, Cary, NC (US); Kent Barclay Howieson, Austin, TX (US); Erdem Matoglu, Austin, TX (US); Bhyrav Murthy Mutnury, Austin, TX (US); Pravin Patel, Cary, NC (US); Nam Huu Pham, Round Rock, TX (US); Caleb James Wesley, Winston Salem, NC (US)

(73) Assignee: International Business Machines Corporation, Armonk, NY (US)

( * ) Notice: Subject to any disclaimer, the term of this patent is extended or adjusted under 35 U.S.C. 154(b) by 158 days.

(21) Appl. No.: 11/875,001

(22) Filed: Oct. 19, 2007

(65) Prior Publication Data

US 2009/0102487 A1    Apr. 23, 2009

(51) Int. Cl.
*G01K 3/00* (2006.01)
*G01J 5/00* (2006.01)
*G01K 17/00* (2006.01)
*G01R 27/32* (2006.01)

(52) U.S. Cl. ............... 324/501; 374/122; 374/137; 702/136; 324/637

(58) Field of Classification Search ............. 324/501, 324/637–648; 374/29, 121, 122, 137; 257/470; 702/130–136
See application file for complete search history.

(56) References Cited

U.S. PATENT DOCUMENTS 4,710,700 A    12/1987    Osaki et al.

5,384,100 A *    1/1995    Freund ............... 422/180

(Continued)

FOREIGN PATENT DOCUMENTS

EP    0 373 069    6/1990

(Continued)

OTHER PUBLICATIONS

V.N Egorov; V.L. Masalov; Yu. A. Nefyodov; A.F. Shevchun; and M.R. Trunin; Measuring Microwave Properties of Laminated Dielectric Substrates, Review of Scientific Instruments, Nov. 2004, 12 pages, vol. 75-Issue 11, American Institute of Physics.

(Continued)

*Primary Examiner*—Timothy J Dole
*Assistant Examiner*—Farhana Hoque
(74) *Attorney, Agent, or Firm*—Cynthia G. Seal; Jeffrey L. Streets

(57) ABSTRACT

A method for testing a printed circuit board to determining the dielectric loss associated with the circuit board material relative to a standard. Dielectric losses in the material generate heat when a high frequency electronic signal, such as a microwave frequency signal, is communicated through a microstrip that is embedded within the printed circuit board. The temperature or spectrum at the surface of printed circuit board is measured and compared against the temperature or spectrum of the standard to determine whether the material under test is acceptable. While various temperature measurement devices may be used, the temperature is preferably measured without contacting the surface, such as using an infrared radiation probe.

12 Claims, 4 Drawing Sheets

U.S. PATENT DOCUMENTS

| | | | |
|---|---|---|---|
| 5,424,633 A * | 6/1995 | Soiferman | 324/158.1 |
| 5,440,566 A | 8/1995 | Spence et al. | |
| 6,320,401 B1 * | 11/2001 | Sugimoto et al. | 324/765 |
| 6,562,448 B1 * | 5/2003 | Chamberlain et al. | 428/312.6 |
| 6,856,140 B2 | 2/2005 | Talanov et al. | |
| 6,873,162 B1 * | 3/2005 | Bois et al. | 324/638 |
| 2004/0164742 A1 * | 8/2004 | Reisinger | 324/501 |

FOREIGN PATENT DOCUMENTS

| EP | 0 921 404 | 6/1999 |
|---|---|---|
| WO | WO 00/77501 | 12/2000 |

OTHER PUBLICATIONS

Biju Kumar; S. Nair; G.M.B. Parkers and P. A. Barnes; G. Bond; Development of novel instrument for microwave dielectric thermal analysis; Review of Scientific Instruments 77, published online Apr. 11, 2006, United Kingdom.

Labourdette, C.; Bourguereau, J.L.; Nonnet, J.C.; Dielectric losses visualization in microstrip antennas by infra-red camera; Institution of Electrical Engineers; publication date 1991; Torino, Italy.

* cited by examiner

METHOD FOR VALIDATING PRINTED CIRCUIT BOARD MATERIALS FOR HIGH SPEED APPLICATIONS

BACKGROUND OF THE INVENTION

1. Field of the Invention

The present invention relates to methods of testing printed circuit board materials for applications involving high-speed communications.

2. Description of the Related Art

A printed circuit board (PCB) is used to mechanically support and electrically connect electronic components using conductive pathways, or traces, etched from copper sheets that have been laminated onto a non-conductive substrate. Populating the board with electronic components forms a printed circuit assembly (PCA), also known as a printed circuit board assembly (PCBA). PCBs are rugged, inexpensive, and can be highly reliable. They require more initial layout effort than either wire-wrapped or point-to-point constructed circuits, but are much cheaper, faster, and consistent in high volume production. Many aspects of PCB design, assembly, and quality control are set by standards that are published by the IPC organization Some PCBs have trace layers inside the PCB and are called multi-layer PCBs. These are formed by bonding together separately etched thin boards. Holes or vias may be formed partially or completely through the PCB by using a drill bit or a laser. Plating or filling a via forms an interconnect that can provide electronic communication between traces in different layers and on the surface.

A communications bus is a subsystem that transfers data or power between computer components inside a computer or between computers. Unlike a point-to-point connection, a bus may logically connect several components over the same set of wires. Most computers have both internal and external buses. An internal bus connects all the internal components of a computer to the motherboard (and thus, the central processing unit and internal memory). These types of buses are also referred to as a local bus, because they are intended to connect to local devices, not to those in other machines or external to the computer. An external bus connects external peripherals to the motherboard.

A modern communications bus transfers data at rates of several gigahertz. At such high speeds, the electronic communications through the bus are subject to dielectric dissipation factor, also known as dielectric loss. Dielectric loss is an intrinsic characteristic of the PCB material. Therefore, the primary approach to controlling the extent of dielectric loss is to carefully select appropriate dielectric materials that will be used in the PCB.

Present approaches taken to qualify materials for PCBs, such as short propagation pulse or corner-corner probing, require expensive equipment and a high level of skill to test properly. Therefore, there is a need for a simple and accurate method for testing a printed circuit board in order to determine whether the dielectric loss of the material is acceptable.

SUMMARY OF THE INVENTION

One embodiment of the present invention provides a method for testing a printed circuit board. The method applies a high frequency electronic signal, most preferably a microwave frequency, to an electronically conductive microstrip embedded within the printed circuit board. The temperature at the surface of the printed circuit board adjacent the embedded microstrip is measured and compared to a setpoint temperature representative of a standard acceptable printed circuit board. Optionally, the microwave signal may be generated using a PCI Express controller chip or a function generator. In a further embodiment, the microstrip is formed to specifications consistent with a high-speed communication bus selected from the group consisting of hyper transport (HT), serial attached SCSI (SAS), serial advanced technology attachment (SATA), and peripheral component interconnect express (PCIe), and the microwave signal emulates a communication signal that would be carried over the communication bus. Further still, the temperature at the surface of the printed circuit board is preferably measured without contacting the surface, such as using an infrared radiation probe.

DETAILED DESCRIPTION OF THE INVENTION

Figure 1:
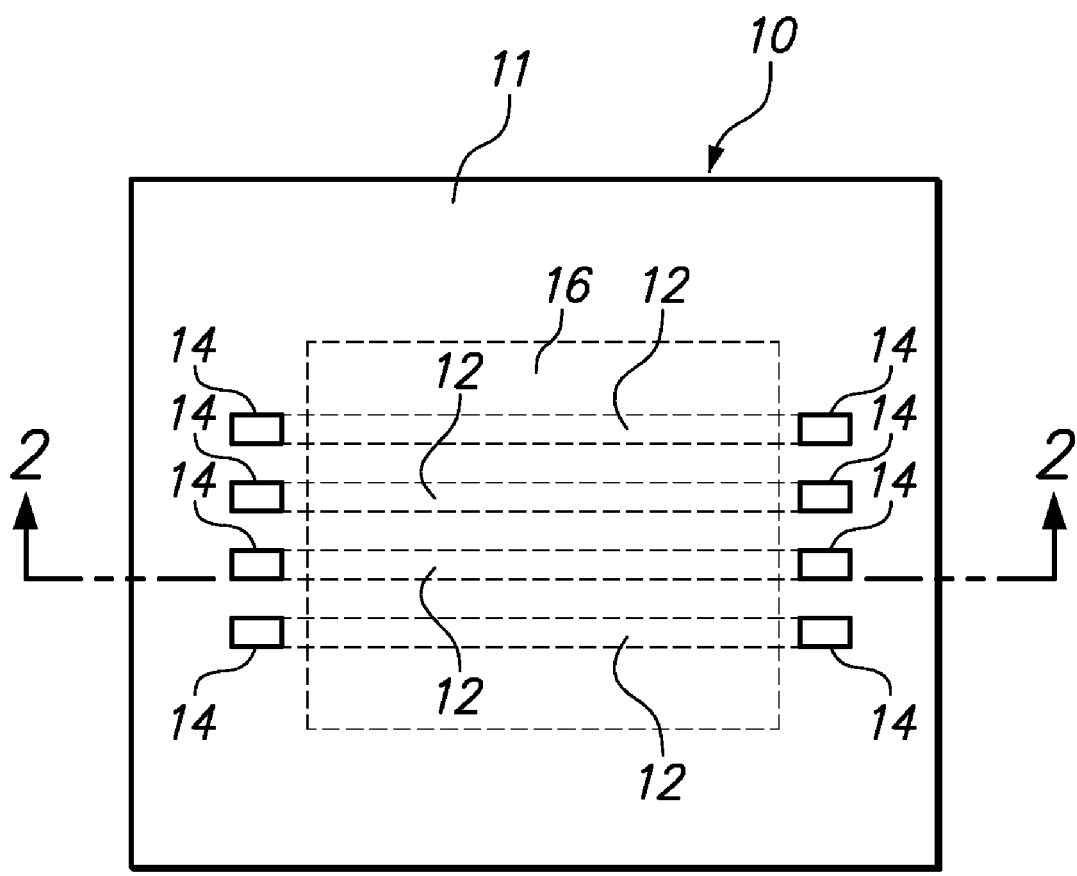
FIG. 1 is a top view of a printed circuit board having four embedded electronically conductive microstrips and a contact pad in electronic communication with the ends of the microstrips.

One embodiment of the present invention provides a method for testing a printed circuit board. The test is beneficial in determining the extent of dielectric loss associated with the material used to make the printed circuit board. When a high frequency electronic signal is communicated through a microstrip that is embedded within the printed circuit board, dielectric losses generate heat that is measurable by an increase in the temperature at the surface of printed circuit board. Comparing the measured temperature or temperature spectrum against the temperature or spectrum of an acceptable standard printed circuit board provides a quick and simple determination whether the material used in the tested printed circuit board is acceptable.

In a specific embodiment, the method applies a high frequency electronic signal to an electronically conductive microstrip embedded within the printed circuit board. The high frequency signal is preferably applied at a microwave frequency, between about 300 megahertz and about 300 gigahertz. However, the most important results are obtained at frequencies near those that are intended to be used within the printed circuit board. Presently, a communication bus embedded in the printed circuit board may operate at a frequency of between about 1 and about 10 gigahertz. However, as speeds increase, the desired testing frequency should be increased similarly in order to obtain results consistent with the intended application.

The temperature at the surface of the printed circuit board adjacent the embedded microstrip is measured while the high frequency electronic signal is being applied. This may include a single steady state temperature measurement or a series of temperature measurements over time. Furthermore, the temperature measurement may be a discrete temperature at a single point on the printed circuit board surface, discrete temperatures at various points over the surface, or a temperature spectrum over the relevant surface area. While various temperature measurement devices may be used, the temperature is preferably measured without contacting the surface, such as using an infrared radiation probe.

The temperature measurement of the printed circuit board under test is compared to temperature data representative of a standard acceptable printed circuit board under similar conditions, such as a similar high frequency signal, similar printed circuit board thickness, similar embedded microstrip, and similar time and location of the measurement. Optionally, the printed circuit board under test may be tested simultaneous to the standard printed circuit board in order that the user can easily assess that the conditions are identical and the comparison is accurate.

Although the comparison may lead to various conclusions or results, the material used to make the printed circuit board under test will be determined as being acceptable and validated if the temperature measurement is less than or equal to the temperature measurement of the standard printed circuit board. Of course, other standards, set points, profiles or spectrums may be established as a basis for a successful comparison.

In a further embodiment, the microstrip is formed to specifications consistent with a high-speed communication bus selected from the group consisting of hyper transport (HT), serial attached SCSI (SAS), serial advanced technology attachment (SATA), and peripheral component interconnect express (PCIe). It may also be desirable to generate and apply a high speed electronic signal that emulates a communication signal that would be carried over one of these or other communication buses, such as by using a PCI Express controller chip or a function generator. Using a standard bus configuration for the microstrip and applying a standard communication signal will assure that the results of the test are representative of results that can be expected in actual use. Another benefit of such a test arrangement is that the testing may be implemented using readily available components and the printed circuit board under test may be manufactured using existing designs and systems.

The sensitivity of the foregoing tests may be improved by preventing the heat generated by dielectric loss from being rapidly dissipated from the printed circuit board into the surrounding environment. Accordingly, insulation or baffles may be used near the printed circuit board to prevent conduction or convection of the heat away from the surface being measured.

FIG. 1 is a top view of a printed circuit board 10 comprising a substrate material 11 having four embedded electronically conductive microstrips 12 and a contact pad 14 in electronic communication with the ends of the microstrips. The contact pads 14 are formed on the top surface of the printed circuit board 10 to facilitate electronic communication between testing equipment and the embedded microstrips 12. An electronically conductive power or ground layer 16 is typically included beneath the microstrips 12 to affect the impedance of the microstrips.

Figure 2:
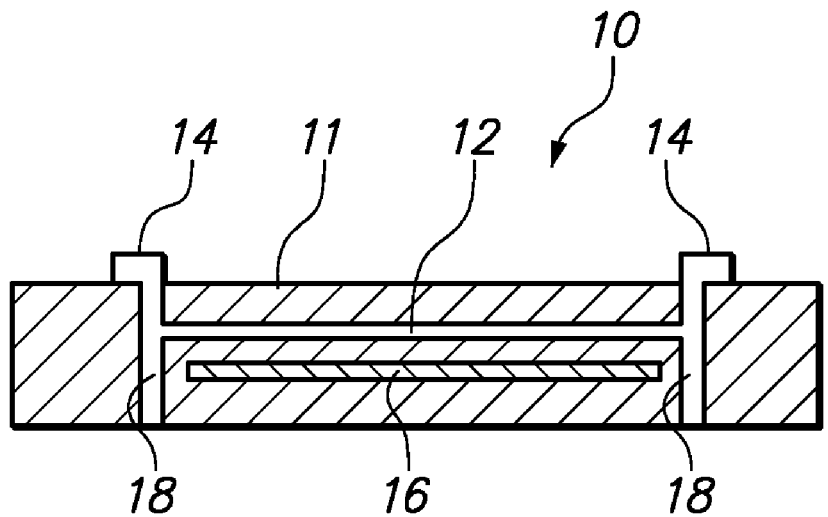
FIG. 2 is a cross-sectional side view of the printed circuit board of FIG. 1 showing an embedded microstrip in electronic communication with two contact pads through a pair of interconnects.

FIG. 2 is a cross-sectional side view of the printed circuit board 10 of FIG. 1 showing a single embedded microstrip 12 in electronic communication with two contact pads 14 through a pair of interconnects 18. Those having ordinary skill in the art are well aware of techniques used to prepare a laminate structure as shown in FIG. 2. Such techniques may include, without limitation, deposition, etching, bonding, drilling, plating, and curing. It should be recognized that only a portion of the interconnect 18 shown is necessary to achieve electronic communication between the pads 14 and the microstrip 12. Having prepared a printed circuit board 10 having one or more embedded microstrip 12 in electronic communication with the contact pads 14, the printed circuit board material 11 may be tested for dielectric loss.

Figure 3:
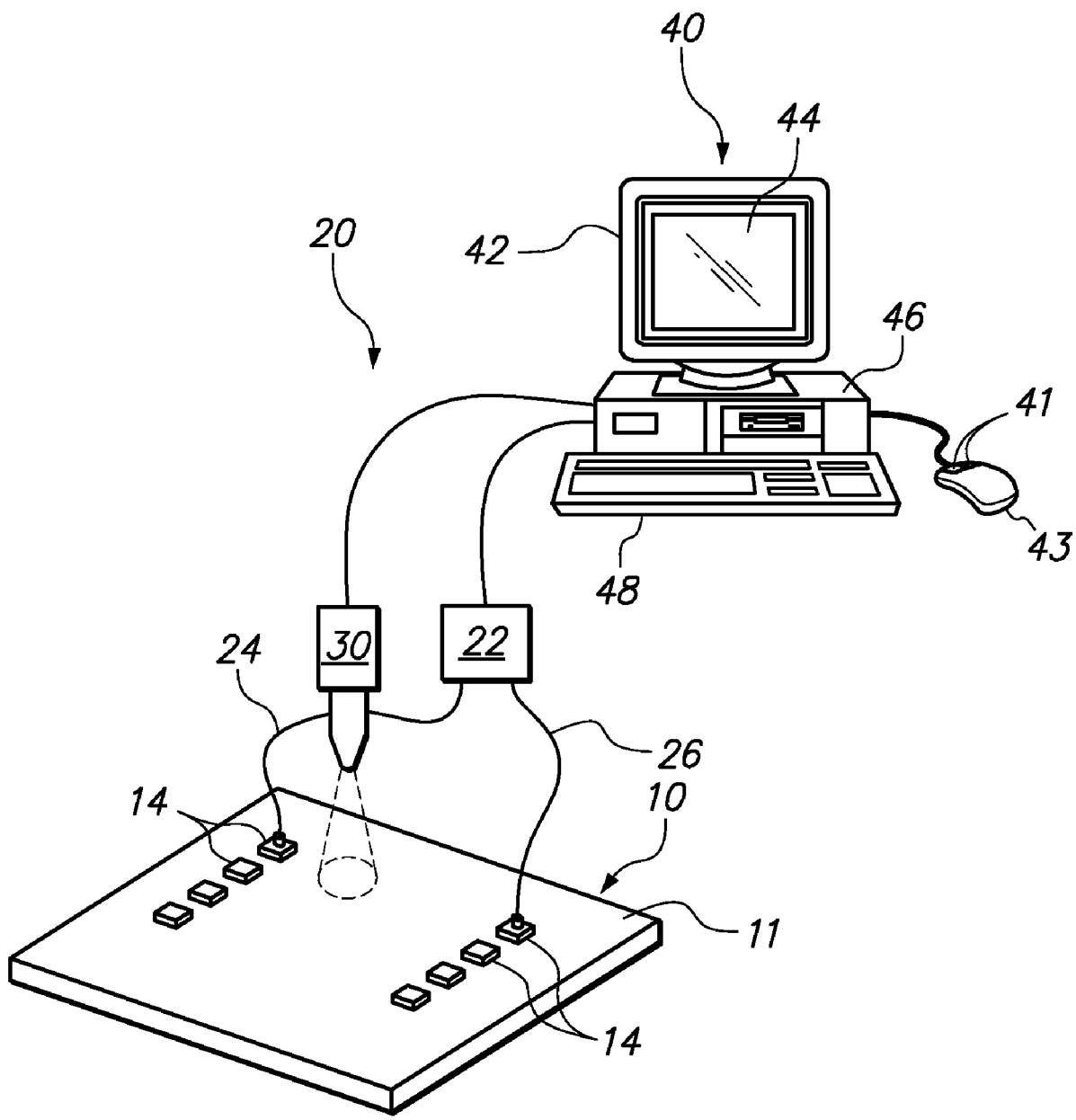
FIG. 3 is a schematic diagram of a system for testing the printed circuit board.

FIG. 3 is a schematic diagram of a system 20 for testing the printed circuit board 10. A function generator or controller chip 22 is coupled to a computer 40 which controls the operation of the device 22. The device 22 then applies a high speed electronic communication signal to pads 14 at the two ends of the same embedded microstrip (not shown) using a pair of leads 24, 26. During the application of the high speed signal, the surface of material 11 heats up due to dielectric losses within the material. An infrared radiation probe 30 is directed toward the surface at a point or region adjacent the embedded microstrip in which dielectric losses are occurring in order to obtain a temperature measurement. The probe 30 provides temperature measurement data to the computer 40 for analysis. Regardless of the form of the temperature measurement, the temperature measurement data is compared against temperature measurement data obtained by testing a standard printed circuit board under the same conditions.

The computer 40 that is capable of controlling the high speed signal generating device 22 and receiving the temperature measurements from the pyrometer 30 includes a display device 42 (such as a monitor), a display screen 44, a cabinet 46 (which encloses components typically found in a computer, such as CPU, RAM, ROM, video card, hard drive, sound card, serial ports, etc.), a keyboard 48, and a mouse 43. The mouse 43 may have one or more buttons, such as buttons 41, to allow a user to provide input through a graphical user interface.

Figure 4:
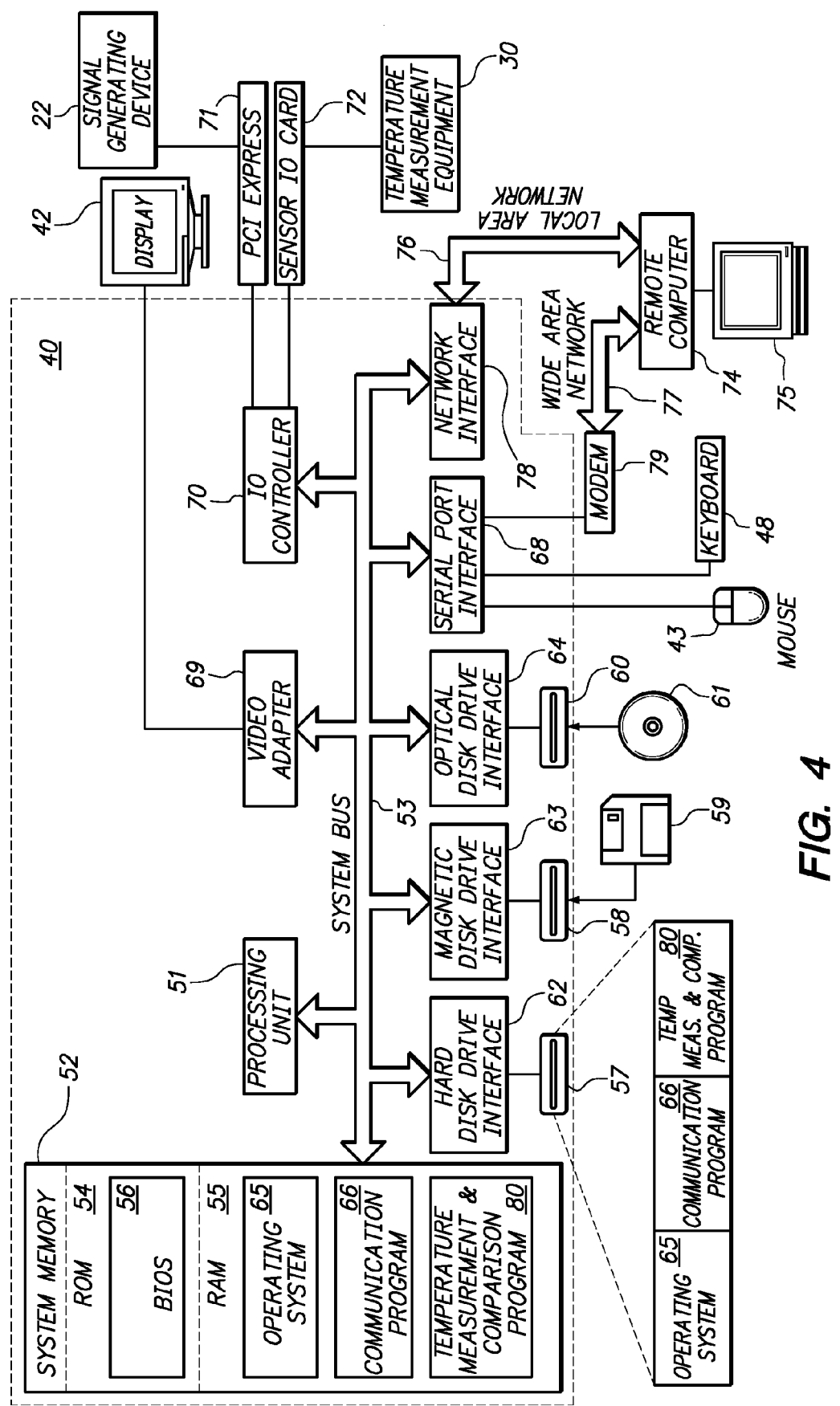
FIG. 4 is a schematic diagram of a computer system suitable for use in the system for monitoring inventory.

FIG. 4 is a schematic diagram of the computer system 40 in one configuration suitable for use in the system for testing printed circuit boards. The system 40 may be a general-purpose computing device in the form of a conventional personal computer. Generally, the personal computer 40 includes a processing unit 51, a system memory 52, and a system bus 53 that couples various system components including the system memory 52 to processing unit 51. System bus 53 may be any of several types of bus structures including a memory bus or memory controller, a peripheral bus, and a local bus using any of a variety of bus architectures. The system memory includes a read-only memory (ROM) 54 and random-access memory (RAM) 55. A basic input/output system (BIOS) 56, containing the basic routines that help to transfer information between elements within personal computer 40, such as during start-up, is stored in ROM 54.

Computer 40 further includes a hard disk drive 57 for reading from and writing to a hard disk, a magnetic disk drive 58 for reading from or writing to a removable magnetic disk 59, and an optical disk drive 60 for reading from or writing to a removable optical disk 61 such as a CD-ROM or other optical media. Hard disk drive 57, magnetic disk drive 58, and optical disk drive 60 are connected to system bus 53 by a hard disk drive interface 62, a magnetic disk drive interface 63, and an optical disk drive interface 64, respectively. Although the exemplary environment described herein employs hard disk 57, removable magnetic disk 59, and removable optical disk 61, it should be appreciated by those skilled in the art that other types of computer readable media which can store data that is accessible by a computer, such as magnetic cassettes, flash memory cards, digital video disks, Bernoulli cartridges, RAMs, ROMs, and the like, may also be used in the exemplary operating environment. The drives and their associated computer readable media provide nonvolatile storage of computer-executable instructions, data structures, program modules, and other data for computer 40. For example, the operating system 65 and application programs, such as a high speed communications program 66 and a temperature measurement and comparison program 80 may be stored in the hard disk 57 or in RAM 55 of the computer 40.

A user may enter commands and information into personal computer 40 through input devices, such as a keyboard 48 and a pointing device, such as a mouse 43. Other input devices (not shown) may include a microphone, joystick, game pad, satellite dish, scanner, or the like. These and other input devices are often connected to processing unit 51 through a serial port interface 68 that is coupled to the system bus 53, but input devices may be connected by other interfaces, such as a parallel port, game port, a universal serial bus (USB), or the like. A display device 42 may also be connected to system bus 53 via an interface, such as a video adapter 69. In addition to the monitor, personal computers typically include other peripheral output devices (not shown), such as speakers and printers.

The computer 40 may operate in a networked environment using logical connections to one or more remote computers 74. Remote computer 74 may be another personal computer, a server, a client, a router, a network PC, a peer device, a mainframe, a personal digital assistant, an Internet-connected mobile telephone or other common network node. While a remote computer 74 typically includes many or all of the elements described above relative to the computer 40, only a memory storage device 75 has been illustrated in the figure. The logical connections depicted in the figure include a local area network (LAN) 76 and a wide area network (WAN) 77. Such networking environments are commonplace in offices, enterprise-wide computer networks, intranets, and the Internet.

When used in a LAN networking environment, the computer 40 is often connected to the local area network 76 through a network interface or adapter 78. When used in a WAN networking environment, the computer 40 typically includes a modem 79 or other means for establishing high-speed communications over WAN 77, such as the Internet. A modem 79, which may be internal or external, is connected to system bus 53 via serial port interface 68. In a networked environment, program modules depicted relative to personal computer 40, or portions thereof, may be stored in the remote memory storage device 75. It will be appreciated that the network connections shown are exemplary and other means of establishing a communications link between the computers may be used. A number of program modules may be stored on hard disk 57, magnetic disk 59, optical disk 61, ROM 54, or RAM 55, including an operating system 65 and browser 66.

The system bus 53 may also communicate with an IO controller 70 that provides an interface to a bus, such as a PCI express bus 71, PCIX bus, or GPIB. A sensor IO adapter card 72 may be plugged into such busses or the IO controller 70 and provide communication with the temperature measurement equipment 30 and provide data to the temperature measurement and comparison program 80. Furthermore, the signal generating device 22, such as a controller chip, may receive instructions from the system 40 through a bus, such as the PCI Express bus 71.

The devices shown in FIG. 4 should not imply that the invention has architectural limitations. For example, those skilled in the art will appreciate that the present invention may be implemented in other computer system configurations, including hand-held devices, multiprocessor systems, microprocessor based or programmable consumer electronics, network personal computers, minicomputers, mainframe computers, and the like. The invention may also be practiced in distributed computing environments, where tasks are performed by remote processing devices that are linked through a communications network. In a distributed computing environment, program modules may be located in both local and remote memory storage devices.

Figure 5:
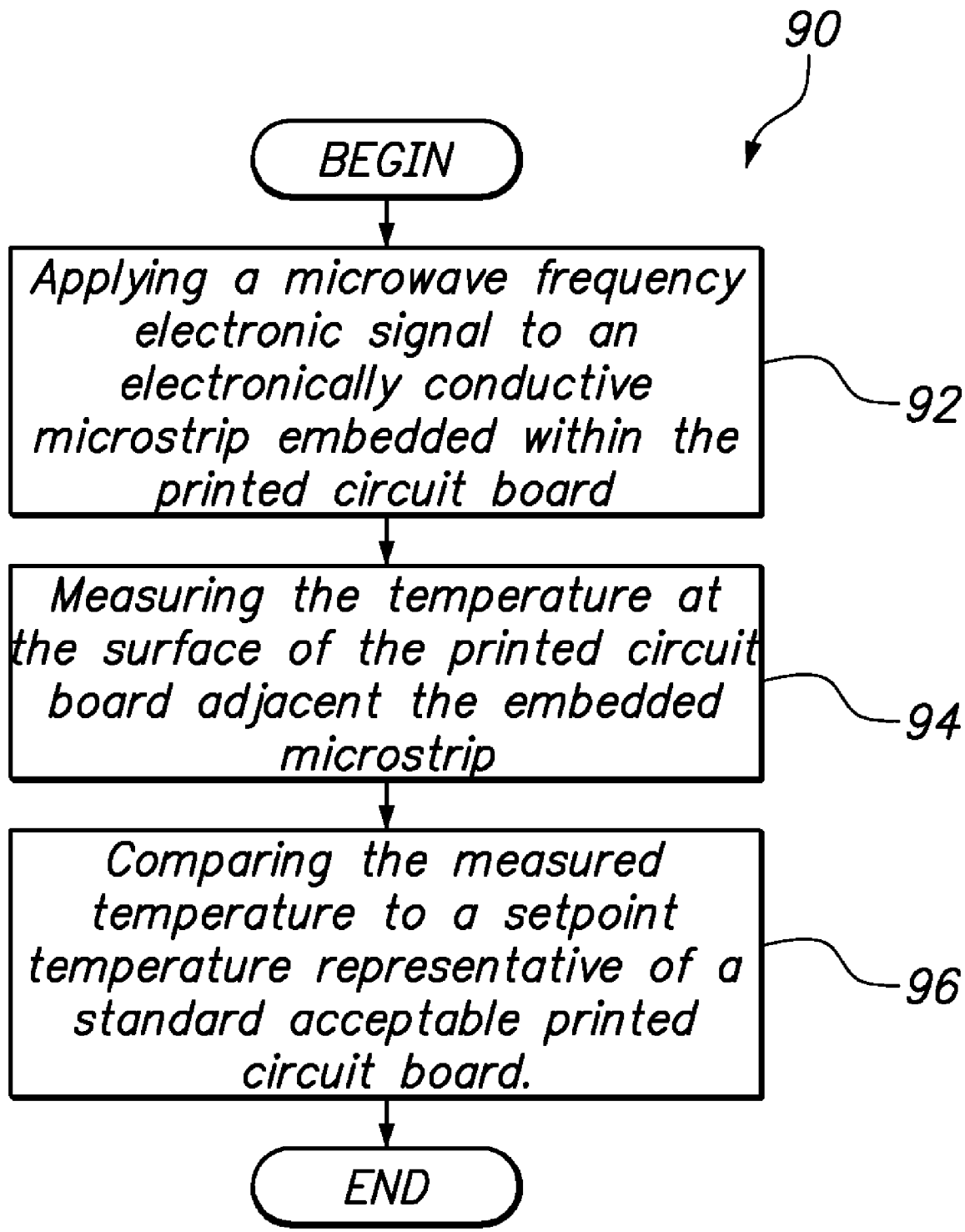
FIG. 5 is a logic diagram of a method for testing a printed circuit board.

FIG. 5 is a logic diagram of a method for testing a printed circuit board. The method may be implemented in a computer readable medium having a computer program product including instructions for carrying out the method. The method 90 includes the steps of applying a microwave frequency electronic signal to an electronically conductive microstrip embedded within the printed circuit board (step 92), measuring the temperature at the surface of the printed circuit board adjacent the embedded microstrip (step 94), and comparing the measured temperature to a setpoint temperature representative of a standard acceptable printed circuit board (step 96).

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for testing a printed circuit board, comprising:
applying a microwave frequency electronic signal to an electronically conductive microstrip embedded within the printed circuit board sufficient to cause dielectric heating;
measuring an increased temperature at the surface of the printed circuit board adjacent the embedded microstrip as a result of applying the microwave frequency electronic signal to the electronically conductive microstrip; and
comparing the measured temperature to a setpoint temperature representative of a standard acceptable printed circuit board.

2. The method of claim 1, wherein the microwave signal emulates a serial bus signal.

3. The method of claim 1, further comprising:
generating the microwave signal using a controller chip.

4. The method of claim 1, further comprising:
generating the microwave signal using a function generator.

5. The method of claim 1, further comprising:
using a baffle near the printed circuit board to insulate the printed circuit board during the temperature measurement to reduce heat dissipation.

6. The method of claim 1, further comprising:
measuring the temperature at the surface, of the standard acceptable printed circuit board at the same time and under the same conditions as measuring the temperature at the surface of the printed circuit board under test.

7. The method of claim 1, further comprising:
forming the microstrip to specifications consistent with a high-speed communication bus selected from the group consisting of hyper transport (HT), serial attached SCSI (SAS), serial advanced technology attachment (SATA), peripheral component interconnect express (PCIe).

8. The method of claim 1, wherein the temperature at the surface of the printed circuit board is measured without contacting the surface.

9. The method of claim 8, wherein the temperature is measured by detecting thermal radiation or infrared radiation.

10. The method of claim 1, wherein the printed circuit board includes an electronically conductive power or ground layer below the microstrip.

11. The method of claim 1, wherein the microwave signal is applied to multiple electronically conductive microstrips embedded within the printed circuit board and operable as a functional serial bus.

12. The method of claim 1, further comprising:
forming an electronically conductive interconnect between the microstrip and the surface of the printed circuit board; and forming an electronically conductive contact pad on the surface of the printed circuit board and in electronic communication with the interconnect.

* * * * *